(12) United States Patent
Suchanek et al.

(10) Patent No.: US 9,321,035 B2
(45) Date of Patent: Apr. 26, 2016

(54) MODIFIED CARRIER FOR SILVER BASED ETHYLENE OXIDE CATALYST

(71) Applicant: Scientific Design Company, Inc., Little Ferry, NJ (US)

(72) Inventors: Wojciech Suchanek, Wyckoff, NJ (US); Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 125 days.

(21) Appl. No.: 14/175,401

(22) Filed: Feb. 7, 2014

(65) Prior Publication Data

US 2014/0221196 A1 Aug. 7, 2014

Related U.S. Application Data

(60) Provisional application No. 61/762,139, filed on Feb. 7, 2013.

(51) Int. Cl.
*B01J 23/66* (2006.01)
*B01J 21/04* (2006.01)
*B01J 23/50* (2006.01)

(52) U.S. Cl.
CPC *B01J 23/66* (2013.01); *B01J 21/04* (2013.01); *B01J 23/50* (2013.01); *Y02P 20/52* (2015.11)

(58) Field of Classification Search
CPC ............ B01J 21/04; B01J 23/66; B01J 23/50; B01J 32/00; B01J 35/0075; B01J 35/10; B01J 37/00; B01J 37/0072
USPC .......... 502/348, 355; 423/131, 132, 625, 626, 423/628
See application file for complete search history.

(56) References Cited

U.S. PATENT DOCUMENTS

| | | | | |
|---|---|---|---|---|
| 3,453,104 | A | * | 7/1969 | De Marchi et al. ............ 419/19 |
| 3,563,914 | A | | 2/1971 | Wattmena |
| 3,628,914 | A | * | 12/1971 | Graulier ........................ 423/628 |
| 3,702,259 | A | | 11/1972 | Nielsen |
| 4,226,782 | A | | 10/1980 | Hayden et al. |
| 4,242,235 | A | | 12/1980 | Cognion et al. |

(Continued)

FOREIGN PATENT DOCUMENTS

| | | | | |
|---|---|---|---|---|
| CN | 102133544 | * | 7/2011 | ............ B01J 27/138 |
| CN | 103357442 | * | 10/2013 | ............... B01J 21/04 |
| WO | 2014/124095 | * | 8/2014 | ................ C01F 7/02 |

OTHER PUBLICATIONS

International Search Report and Written Opinion dated May 19, 2014 received in a corresponding foreign application.

(Continued)

*Primary Examiner* — Patricia L Hailey
(74) *Attorney, Agent, or Firm* — Scully, Scott, Murphy & Presser, P.C.

(57) ABSTRACT

Silver based ethylene oxide catalysts having enhanced stability are disclosed. The enhanced stability silver based ethylene oxide catalysts include an alumina carrier which has been modified to include cavities on the surface of the carrier. The presence of the cavities on the surface of the modified carrier stops or at least impedes the motion of silver particles on the surface of the carrier during an epoxidation process. In particular, the cavities on the surface of the alumina carrier effectively trap and/or anchor silver particles and prevent them from further motion.

37 Claims, 3 Drawing Sheets

(56) References Cited

U.S. PATENT DOCUMENTS

| | | | |
|---|---|---|---|
| 4,761,394 | A | 8/1988 | Lauritzen |
| 4,766,105 | A | 8/1988 | Lauritzen |
| 4,908,343 | A | 3/1990 | Bhasin |
| 5,011,807 | A | 4/1991 | Hayden et al. |
| 5,057,481 | A | 10/1991 | Bhasin |
| 5,099,041 | A | 3/1992 | Hayden et al. |
| 5,102,848 | A | 4/1992 | Soo et al. |
| 5,112,795 | A | 5/1992 | Minahan et al. |
| 5,187,140 | A | 2/1993 | Thorsteinson et al. |
| 5,266,548 | A | 11/1993 | Koradia et al. |
| 5,380,697 | A | 1/1995 | Matusz et al. |
| 5,407,888 | A | 4/1995 | Herzog et al. |
| 5,597,773 | A | 1/1997 | Evans et al. |
| 5,831,037 | A | 11/1998 | Ohsuga et al. |
| 6,831,037 | B2 | 12/2004 | Szymanski et al. |
| 7,507,844 | B2 * | 3/2009 | Pak .............................. 549/534 |
| 2004/0110973 | A1 | 6/2004 | Matusz |
| 2005/0096219 | A1 | 5/2005 | Szymanski et al. |
| 2006/0293180 | A1 | 12/2006 | Thorsteinson |
| 2007/0207084 | A1 * | 9/2007 | Zachariah et al. ......... 423/592.1 |
| 2007/0280877 | A1 | 12/2007 | Suchanek et al. |
| 2011/0301368 | A1 | 12/2011 | Pak et al. |
| 2012/0065055 | A1 * | 3/2012 | Jiang et al. .................... 502/216 |

OTHER PUBLICATIONS

Drake, L.C., et al., "Macropore-Size Distributions in Some Typical Porous Substances", Ind. Eng. Chem. Anal. Ed., Publication Date: Dec. 1945, 17 (12), pp. 787-791.

Brunauer, S., et al., "Adsorption of Gases in Multimolecular Layers", J. Am. Chem. Soc., Feb. 1938, pp. 309-316.

* cited by examiner

MODIFIED CARRIER FOR SILVER BASED ETHYLENE OXIDE CATALYST

CROSS REFERENCE TO RELATED APPLICATION

The present invention claims the benefit of U.S. Provisional Patent Application No. 61/762,139 filed Feb. 7, 2013, the entire content and disclosure of which is incorporated herein by reference.

FIELD OF THE INVENTION

The present disclosure relates to silver based ethylene oxide catalysts, and more particularly, to carriers for such catalysts.

BACKGROUND

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., carrier). Typically, one or more promoters are included in the catalyst to improve or adjust properties of the catalyst, such as selectivity.

Generally, but not necessarily always, HSCs achieve the higher selectivity (typically, in excess of 87 mole % or above) by incorporation of rhenium as a promoter. Typically, one or more additional promoters selected from alkali metals (e.g., cesium), alkaline earth metals, transition metals (e.g., tungsten compounds), and main group metals (e.g., sulfur and/or halide compounds) can also be included.

There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts typically exhibit selectivities of at least 83 mole % and up to 87 mole %.

It is well known that with extended use of a catalyst, the catalyst will age (i.e., degrade) to a point until use of the catalyst is no longer practical. There is thus a continuous effort to extend the useful lifetime (i.e., "longevity" or "usable life") of catalysts. The useful lifetime of the catalyst is directly dependent on the stability of the catalyst. As used herein, the "useful lifetime" is the time period for which a catalyst can be used until one or more of its functional parameters, such as selectivity or activity, degrade to such a level that use of the catalyst becomes impractical.

Stability of the catalyst has largely been attributed to various characteristics of the carrier. Some characteristics of the carrier that have undergone much research include carrier formulation, surface area, porosity, and pore volume distribution, among others.

The most widely used formulation for the carriers of ethylene epoxidation catalysts are those based on alumina, typically alpha-alumina. Much research has been directed to investigating the effect of the alumina composition for improving stability and other properties of the catalyst. The preparation and modification of alumina carriers for enhancing ethylene epoxidation catalyst performance are described, for example, in U.S. Pat. Nos. 4,226,782, 4,242,235, 5,266,548, 5,380,697, 5,597,773, 5,831,037 and 6,831,037 as well as in U.S. Patent Application Publication Nos. 2004/0110973 A1 and 2005/0096219 A1.

However, there remains a need in the art for further improvements in the stability of ethylene epoxidation catalysts. There is a particular need for improving the stability of such catalysts by modifying the carrier by means that are facile and financially feasible.

SUMMARY

Silver based ethylene oxide catalysts having enhanced stability are disclosed. The enhanced stability silver based ethylene oxide catalysts of the present disclosure include an alumina carrier which has been modified to include artificially created cavities on the surface of the carrier. The presence of the cavities on the surface of the modified carrier stops or at least impedes the motion of silver particles on the surface of the carrier during an epoxidation process. In particular, the cavities on the surface of the alumina carrier effectively trap and/or anchor silver particles and prevent them from further motion.

In one aspect of the present disclosure, a method of forming an alumina carrier having artificially formed cavities present on the surface thereof is provided. The method of the present disclosure includes providing an admixture of reactive particles dispersed on a surface of alumina particles. In accordance with the present disclosure, the reactive particles comprise a different material than the alumina particles. The admixture is then formed into a predetermined shape and thereafter it is sintered to form an alumina carrier having the predetermined shape and comprising sacrificial particles located on the surface and embedded within a portion of each alumina particle. In accordance with the present disclosure, each sacrificial particle comprises a material containing an element of the reactive particle-Al—O, has a different phase than the alumina particles, and has a higher solubility in a solvent than the alumina particles. Next, at least a portion of the sacrificial particles is removed from each of the alumina particles using the solvent to form cavities in the surface of each of the alumina particles.

In another aspect of the present disclosure, a method of preparing a silver based ethylene oxide catalyst is provided. This aspect of the present disclosure includes forming an alumina carrier by steps of (i) providing an admixture of reactive particles dispersed on a surface of alumina particles, wherein the reactive particles comprise a different material than the alumina particles; (ii) forming the admixture into a predetermined shape; (iii) sintering the admixture to form an alumina carrier having the predetermined shape and comprising sacrificial particles located on the surface and embedded within a portion of each alumina particle, wherein each sacrificial particle comprises a material containing an element of the reactive particle-Al—O, has a different phase than the alumina particles, and has a higher solubility in a solvent than the alumina particles; and (iv) removing at least a portion of the sacrificial particles from each of the alumina particles using the solvent to form cavities in the surface of each of the alumina particles. After providing the alumina carrier, at least a catalytic effect amount of silver is deposited on the alumina carrier.

In a further aspect of the present disclosure, a carrier is provided that contains artificially formed cavities therein. The carrier of the present disclosure comprises a plurality of bound alumina particles, wherein each alumina particle contains a plurality of cavities located within a surface of the alumina particle, and wherein each cavity has a dimension from 2 nm to 5 microns.

In a yet further aspect of the present disclosure, an ethylene epoxidation catalyst is provided. In accordance with this aspect of the present disclosure, the catalyst comprises a carrier comprising a plurality of bound alumina particles, wherein each alumina particle contains a plurality of cavities located within a surface of the alumina particle, and wherein each cavity has a dimension from 2 nm to 5 microns. The catalyst further includes a catalytic amount of silver and a promoting amount of one or more promoters deposited on and/or in the carrier.

DETAILED DESCRIPTION

Figure 1A:
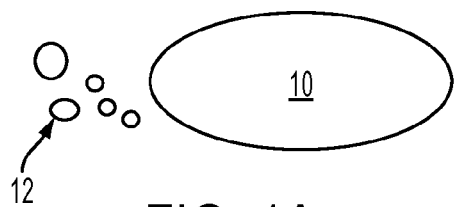
FIGS. 1A-1E are schematic drawings showing the basic processing steps of the present disclosure.

The present disclosure provides an improved alumina carrier for an ethylene epoxidation catalyst. The carrier is improved in that it imparts an enhanced stability to a silver based catalyst derived therefrom. By 'enhanced stability' it is meant that the silver based catalysts supported on the carrier of the present disclosure have longer usable lifetimes, and particularly, a significantly reduced degradation in selectivity as compared to an equivalent catalyst supported on a carrier which is not formed in accordance with the present disclosure (i.e., a carrier without intentionally formed cavities), over equivalent time periods of usage.

Without wishing to be bound by any theory, the problem of stability in silver based ethylene oxide catalysts can be associated with coalescene and growth of silver particles on the surface of an aluminum carrier. During the motion of the silver particles on the carrier surface, and while the catalyst is on feed, the silver particles gradually become larger, which results in the loss of active catalyst surface. Such an effect may be responsible for loss of catalyst activity and/or selectivity.

The present disclosure provides alumina carriers which have been modified to include intentionally engineered cavities on the surface of the carrier. The presence of the cavities on the surface of the modified carrier stops or at least impedes the motion of silver particles on the surface of the carrier during an epoxidation process. In particular, the cavities on the surface of the alumina carrier effectively trap and/or anchor silver particles and prevent them from further motion.

The modified alumina carriers of the present disclosure comprise a plurality of bound alumina particles, wherein each alumina particle contains a plurality of cavities located within a surface of the alumina particle, wherein each cavity has a dimension from 2 nm to 5 microns. In some embodiments of the present disclosure, the dimension of each cavity is from 50 nm to 2 microns. In either embodiment, the dimension of the cavities is sufficient to trap at least one silver particle when a catalyst containing the carrier of the present disclosure is used in an epoxidation process. Other dimensions that are lesser than or greater than the above ranges can also be employed as long as the cavities that are intentionally formed are capable of trapping at least one silver particle when a catalyst containing the carrier of the present disclosure is used in an epoxidation process. In some embodiments and in which non-alumina particles are used to form other carriers besides alumina carriers, the other carriers that can be formed in the present disclosure include a plurality of bound non-alumina particles (i.e., silica), wherein each non-alumina particle contains a plurality of cavities located within a surface of the non-alumina particle, wherein each cavity has a dimension from 2 nm to 5 microns.

It is observed that the cavities of the present disclosure are formed after sintering and are present in the surface of individual alumina particles of the carrier. The cavities that are intentionally formed in the present disclosure are different from pores which are formed during sintering but before removing the sacrificial particles of the present disclosure from the alumina particles. Pores are voids/spaces that are formed in the carrier between at least some of the individual alumina particles.

The surface modified carrier of the present disclosure is typically porous and has a B.E.T. surface area of at most 20 $m^2/g$. More typically, the B.E.T. surface area of the carrier of the present disclosure is in the range from about 0.1 to about 10 $m^2/g$, and even more typically the B.E.T. surface area of the carrier of the present disclosure is from about 0.2 to about 3 $m^2/g$. In other embodiments, the surface modified carriers of the present disclosure are characterized by having a B.E.T. surface area from about 0.3 $m^2/g$ to about 3 $m^2/g$, and preferably from about 0.5 $m^2/g$ to about 2.0 $m^2/g$. The B.E.T. surface area described herein can be measured by any suitable method, but is more preferably obtained by the method described in Brunauer, S., et al., *J. Am. Chem. Soc.*, 60, 309-16 (1938).

The carriers of the present disclosure can also be characterized as having a water pore volume from about 0.10 cc/g to about 0.80 cc/g. More typically, the carriers of the present disclosure can also be characterized as having a water pore volume from about 0.20 cc/g to about 0.60 cc/g.

The carriers of the present disclosure can have any suitable distribution of pore diameters. As used herein, the "pore diameter" is used interchangeably with "pore size". Typically, the pore diameters are at least about 0.01 microns (0.01 µm), and more typically, at least about 0.1 µm. In different embodiments, the pore diameters can be at least about 0.2 µm, or 0.3 µm. Typically, the pore diameters are no more than about 50-100 µm. The pore volume and pore size distribution described herein can be measured by any suitable method, but are more preferably obtained by the conventional mercury porosimeter method as described in, for example, Drake and Ritter, "Ind. Eng. Chem. Anal. Ed.," 17, 787 (1945).

The carriers of the present disclosure can have monomodal or multimodal pore size distributions, such as, for example, bimodal. Without wishing to be bound by any theory, it is believed that a catalyst with a bimodal pore size distribution possesses a type of pore structure in which reaction chambers are separated by diffusion channels.

The alumina carriers of the present disclosure also exhibit an average crush strength of from 5 pounds to 50 pounds, with an average crush strength of from 8 pounds to 20 pounds being more typical. The term "average crush strength" denotes an arithmetic average number calculated from individual crush strength measurements for each particle. Crush strength can be determined using ASTM D6175-03(2008) standard method.

Figure 1B:
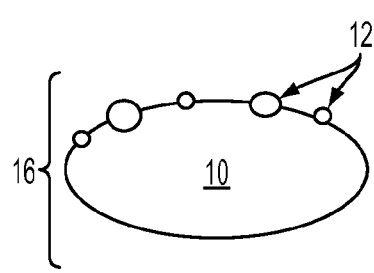
Figure 1C:
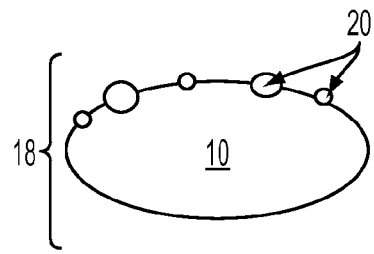
Figure 1D:
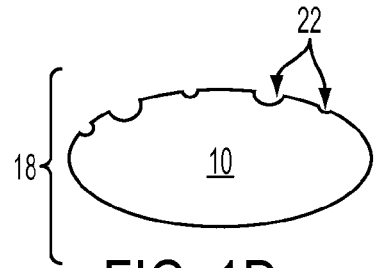
Figure 1E:
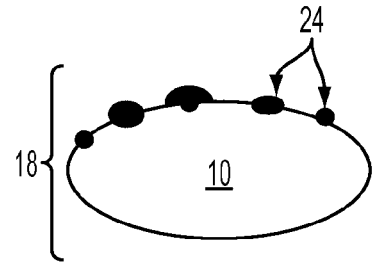

Reference is now made to FIGS. 1A-1E which are schematic illustrations of the process of the present disclosure; the details of the process and materials used will be described herein below. Specifically, FIG. 1A illustrates a step of selecting alumina particles 10 and reactive particles 12; FIG. 1B illustrates the results of forming an admixture 16 and providing a predetermined shape to the admixture (as shown the admixture includes shaped alumina particles 10 having reactive particles 12 dispersed on a surface thereof); FIG. 1C illustrates the admixture 16 after sintering which forms an alumina carrier 18 having the predetermined shape and comprising sacrificial particles 20 located on the surface and embedded within a portion of each alumina particle 10; FIG. 1D illustrates the alumina carrier 18 after removing at least a portion of each sacrificial particle 20 from the carrier creating artificially formed cavities 22 in the alumina particles 10; and FIG. 1E illustrates the carrier of FIG. 1D after silver deposition and use in ethylene oxide; element 24 denotes silver particles which can become trapped and/or anchored in the cavities 22. The same general schematic also applies to cases in which non-alumina carriers are formed.

The alumina carriers of the present disclosure can be prepared by first providing an admixture of reactive particles dispersed on a surface of alumina particles. The alumina particles that can be used in preparing the alumina carrier of the present disclosure are composed of any of the refractory alumina particles known in the art for use in ethylene oxidation catalysts. Preferably, the alumina particles comprise alpha-alumina particles. In one embodiment, the alpha-alumina particles can have a purity of about 80% or greater. In another embodiment, the alpha-alumina particles used in the present disclosure can have a very high purity, i.e., about 95% or more, and more preferably, 98 wt. % or more alpha-alumina. In some embodiments, the alpha-alumina particles are a low sodium alumina. Generally, a "low sodium alumina" material contains 0.1% or less sodium content. Alternatively, or in addition, a "low sodium alumina" can indicate an alumina material having 0.1 mg or less of sodium.

In some embodiments, the admixture may contain particles containing other phases of alumina besides alpha-alumina, such as, for example, gamma-alumina, and/or beta-alumina. In yet other embodiments, the admixture may contain silica, mullite, and/or alkali metal oxides. The admixture may also include other metal-containing and/or non-metal contacting additives and/or impurities which differ from the reactive particles of the present disclosure.

It is noted that in some embodiments, other carriers such as, for example, charcoal, pumice, magnesia, zirconia, titania, kieselguhr, fuller's earth, silicon carbide, silica, silicon carbide, silicon dioxide, clays, artificial zeolites, natural zeolites, and ceramics can be prepared using the processing steps of the present disclosure, i.e., providing an admixture of carrier particles and reactive particles, forming the admixture into a predetermined shape, sintering the admixture forming sacrificial particles that are soluble on the surface of the carriers and include at least an element of the reactive particle and at least an element of the carrier particle, and removing the sacrificial particles. It should be noted that although the description that follows specifically illustrates the preparation of alumina carriers having intentionally formed cavities formed at the surface thereof, the same processing can be used in forming non-alumina carriers by substituting the alumina particles with non-alumina carrier particles.

With respect to alumina carriers and in one embodiment of the present disclosure, all of the alumina particles that can be employed have a particle size from 0.1 μm to 200 μm. The particles can be in form of individual crystallites or larger aggregates and/or agglomerates. In another embodiment of the present disclosure, all of the alumina particles, both as individual crystallites and aggregates, that can be employed have a particle size from 0.1 μm to 200 μm. In some embodiments of the present disclosure, the alumina carrier can be prepared by selecting first alumina particles having a first particle size from 0.5 μm to 50 μm, and second alumina particles having a second particle size, which differ from the first particle size, and are from 5 μm to 200 μm. Additional alumina particles having other particle sizes that are greater than or lesser than the ranges mentioned above for the first and second particle sizes can also be employed in the present disclosure.

In embodiments when alumina particles having different particle sizes are used in preparing the alumina carrier of the present disclosure, the ratio of the alumina particles having the different particle sizes can be varied to achieve a desired carrier property.

The particle sizes given above can refer to a diameter for the case where the particle is spherical or approximately spherical. For cases where the particles substantially deviate from a spherical shape, the particle sizes given above are based on the equivalent diameter of the particles. As known in the art, the term "equivalent diameter" is used to express the size of an irregularly-shaped object by expressing the size of the object in terms of the diameter of a sphere having the same volume as the irregularly-shaped object.

As stated above, the admixture also includes reactive particles dispersed on the surface of the alumina particles. The term "reactive particles" is used herein to denote a material that has a different composition than that of the alumina particles and which, when reacted with the alumina particles during sintering, forms a solid state reaction product with a contacting surface of the alumina particles. This solid state reaction product can be referred to herein as a sacrificial particle since at least a portion of the sacrificial particle can be intentionally removed from the alumina particles forming cavities within each of the individual particles of the alumina carrier of the present disclosure.

In one embodiment of the present disclosure, the reactive particles comprise metal oxide particles. In this embodiment of the present disclosure, the metal oxide reactive particles may comprise zinc (Zn) oxide, calcium (Ca) oxide, magnesium (Mg) oxide and/or boron (B) oxide. In one preferred example, zinc oxide is used as the reactive particles and are dispersed on the surface of the alumina particles.

In another embodiment of the present disclosure, the reactive particles comprise non-oxide particles such as, for example, native metals, sulfides, sulfates, carbonates, carbides, and/or nitrides.

In yet another embodiment of the present disclosure, a fraction of the reactive particles can comprise metal oxide reactive particles, while another fraction of the reactive particles can comprise non-oxide particles.

Notwithstanding the type of reactive particles employed, the reactive particles are dispersed onto the surface of the alumina particles such that the reactive particles do not cover the entire surface of each of the alumina particles. In one embodiment of the present disclosure, from 1 weight percent to 10 weight percent of reactive particles are dispersed onto the surface of the alumina particles. In another embodiment of the present disclosure, from 4 weight percent to 8 weight of reactive particles are dispersed onto the surface of the alumina particles. In either embodiment, the weight percent of reactive particles dispersed on the surface of the alumina particles is based on the total weight of the alumina particles employed.

In one embodiment of the present disclosure, the admixture can be made by mixing, in any order, a solution of reactive particles and a plurality of preselected alumina particles. In such an embodiment, the solution of reactive particles comprises a solvent in which the reactive particles can be provided in the form of a dispersion. Examples of solvents that can be employed in this embodiment of the present disclosure include, but are not limited to, water, alcohols, and/or glycols.

In another embodiment of the present disclosure, the admixture can be made by mixing, in any order, a solution of preselected alumina particles and reactive particles. In such embodiment, the solution of preselected alumina particles comprises a solvent in which the alumina particles can be provided in the form of a dispersion. Examples of solvents that can be employed in this embodiment of the present disclosure include, but are not limited to, water, alcohols, and/or glycols.

In yet another embodiment, the admixture can be made by mixing, in any order, a solution of reactive particles and a solution containing a plurality of preselected alumina particles.

In a further embodiment of the present disclosure, the admixture can be formed by mixing, in any order, dry reactive particles and dry alumina particles.

In another embodiment of the present invention, the reactive particles can be added as a gel, (co)precipitated colloidal particles, or impregnated from salts dissolved in a solution.

In some embodiments, the mixing step used in forming the admixture can be performed at room temperature (20° C.-40° C.). In other embodiments, the mixing step used in forming the admixture can be performed at a temperature up to, but not beyond, the boiling point of any solvent using in forming the admixture.

In some embodiments, the reactive particles can have a particle size that differs from the alumina particles. In other embodiments, the reactive particles can have a same particle size as that of the alumina particles. In further embodiments, a fraction of the reactive particles can have a particle size that differs from the alumina particles, while another fraction of the reactive particles can have a particle size that is the same as that of the alumina particles. In one embodiment of the present disclosure, the reactive particles have a particle size from 10 nm to 300 nm. In another embodiment of the present disclosure, the reactive particles have a particle size from 500 nm to 2 microns. In some embodiments, the reactive particles can all have the same particle size. In another embodiment of the present disclosure, a fraction of the reactive particles can have a first particle size, while at least one other fraction of the reactive particles can have a second particle size which differs from the first particle size.

The admixture may also include a temporary binder or burnout material, a permanent binder, and/or a porosity controlling agent. As stated above, and in some embodiments, the admixture may also include particles of other phases of alumina, silica, mullite, alkali metal oxides (e.g., sodium oxide) and trace amounts of other metal-containing and/or non-metal-containing additives or impurities.

Examples of temporary binders, or burnout materials, include cellulose, substituted celluloses, e.g., methylcellulose, ethylcellulose, and carboxyethylcellulose, stearates (such as organic stearate esters, e.g., methyl or ethyl stearate), waxes, granulated polyolefins (e.g., polyethylene and polypropylene), walnut shell flour, and the like, which are decomposable at the temperatures employed. The binders are responsible for imparting porosity to the carrier material. Burnout material is used primarily to ensure the preservation of a porous structure during the green (i.e., unfired phase) in which the mixture may be shaped into particles by molding or extrusion processes. Burnout materials are essentially completely removed during the sintering step of the present disclosure.

Examples of permanent binders include, for example, inorganic clay-type materials, such as silica and an alkali metal compound. A convenient binder material which may be incorporated with the alumina particles is a mixture of boehmite, an ammonia-stabilized silica sol, and a soluble sodium salt.

The admixture of the present disclosure is then formed into a predetermined shape utilizing conventional methods known in the art. For example, the shaping of the admixture can be performed by extruding, pressing and molding. Other processes that are capable of shaping the admixture and which are typically used in forming carriers for ethylene epoxidation catalysts can also be employed. The predetermined shape that can be formed in the present disclosure includes, but is not limited to, particles, chunks, pellets, rings, spheres, three-holes, wagon wheels, cross-partitioned hollow cylinders, and the like, of a size preferably suitable for employment in fixed bed reactors. In one embodiment, the surface modified carriers of the present disclosure have equivalent diameters in the range of from about 3 mm to about 12 mm, and more typically in the range of from about 5 mm to about 10 mm, which are usually compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object.

After providing the admixture and shaping the same, the admixture containing the predetermined shape is then subjected to a sintering process. During sintering, an alumina carrier having the predetermined shape is formed that contains a plurality of bound alumina particles. Also during sintering, each reactive particle that is in contact with a surface of an alumina particle reacts forming a solid-state reaction product between the contacting reactive particle and the alumina particle, which embeds in the surface of the alumina particle. The solid state reaction product is referred to herein as a sacrificial particle since at least a portion thereof will be subsequently removed from the bound alumina particles of the present disclosure.

Each sacrificial particle that is formed in the present disclosure during sintering comprises a material containing an element of the reactive particle-Al—O. For example, when the reactive particle is a metal oxide, the sacrificial particles comprise a material containing M-Al—O wherein M is zinc (Zn), calcium (Ca), magnesium (Mg), and/or boron (B).

Each sacrificial particle that is formed also has a different phase than the alumina particles. For example, and in one embodiment of the present disclosure, the sacrificial particles can comprise a Zn—Al—O phase.

In addition, each sacrificial particle that is formed has a higher solubility in a solvent than the alumina particles such that during subsequent contact with the solvent at least a portion of the sacrificial particles can be removed from the alumina particles.

The sintering process which is used in forming the alumina carrier containing the sacrificial particles embedded within bound alumina particles can be performed in air and at a temperature from 1000° C. to 1600° C. In another embodiment, the sintering process can be performed in air and at a temperature from 1200° C. to 1500° C. The duration of the sintering process can vary with shorter times being typically associated with higher sintering temperature.

After sintering and forming the alumina carrier, at least a portion of the sacrificial particles are removed from each of the alumina particles using a solvent to form cavities in the surface of each of the alumina particles. In some embodiments, an entirety of each sacrificial particle is removed from the cavities that are present on the surface of the alumina particles to expose a surface of the alumina particles which is located beneath the original uppermost surface of the alumina particles.

In one embodiment, the solvent that is used in removing at least a portion of the sacrificial particles from the alumina particles comprises an aqueous alkaline solution. Examples of aqueous alkaline solutions that can be employed in the present disclosure include, but are not limited to NaOH, KOH, and CsOH.

In another embodiment, the solvent that that is used in removing at least a portion of the sacrificial particles from the alumina particles comprises an aqueous acidic solution. Examples of aqueous acid solutions that can be employed in the present disclosure include, but are not limited to HCl, $H_2SO_4$, HF, and $HNO_3$.

In another aspect, the present disclosure is directed to an ethylene epoxidation catalyst produced from the surface modified carrier described above. In order to produce the catalyst, a modified carrier having the above characteristics is then provided with a catalytically effective amount of silver thereon and/or therein. The catalyst can be prepared by impregnating the modified carrier of the present disclosure with silver ions, compounds, complexes, and/or salts dissolved in a suitable solvent sufficient to cause deposition of silver precursor compound onto and/or into the carrier. In some embodiments, and as will be described in greater detail herein below, the carrier can be impregnated and incorporated with rhenium and silver, along with any desired promoters, by any of the conventional methods known in the art, e.g., by excess solution impregnation, incipient wetness impregnation, spray coating, and the like. Typically, the carrier material is placed in contact with the silver-containing solution until a sufficient amount of the solution is absorbed by the carrier. Infusion of the silver-containing solution into the carrier can be aided by application of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In one embodiment, the solution comprises an aqueous solution of silver oxalate and ethylene diamine. The complexing/solubilizing agent may be present in the impregnating solution in an amount from about 0.1 to about 10 moles of ethylene diamine per mole of silver, preferably from about 0.5 to about 5 moles, and more preferably from about 1 to about 4 moles of ethylene diamine for each mole of silver.

The concentration of silver salt in the solution is typically in the range from about 0.1% by weight to the maximum permitted by the solubility of the particular silver salt in the solubilizing agent employed. More typically, the concentration of silver salt is from about 0.5% to 45% by weight of silver, and even more typically, from about 5 to 35% by weight.

Any one or more promoting species in a promoting amount can be incorporated into the carrier either prior to, coincidentally with, or subsequent to the deposition of the silver. As used herein, a "promoting amount" of a certain component refers to an amount of that component that works effectively to provide an improvement in one or more of the catalytic properties of a subsequently formed catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

For example, catalysts that are based on the carrier described above may include a promoting amount of an alkali metal or a mixture of two or more alkali metals. Suitable alkali metal promoters include, for example, lithium, sodium, potassium, rubidium, cesium or combinations thereof. In one embodiment, cesium can be employed. In another embodiment, combinations of cesium with other alkali metals can be employed. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the alkali metal.

The catalyst that is based on carrier of the present disclosure may also include a promoting amount of a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The catalyst that is based on the carrier of the present disclosure may also include a promoting amount of a main group element or a mixture of two or more main group elements. Suitable main group elements include any of the elements in Groups IIIA (boron group) to VIIA (halogen group) of the Periodic Table of the Elements. For example, the carrier can include a promoting amount of one or more sulfur compounds, one or more phosphorus compounds, one or more boron compounds, one or more halogen-containing compounds, or combinations thereof. The carrier can also include a main group element, aside from the halogens, in its elemental form.

The catalyst that is based on the carrier of the present disclosure may also include a promoting amount of a transition metal or a mixture of two or more transition metals. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the transition metal is an early transition metal, i.e., from Groups IIIB, IVB, VB or VIB, such as, for example, hafnium, yttrium, molybdenum, tungsten, rhenium, chromium, titanium, zirconium, vanadium, tantalum, niobium, or a combination thereof.

In one embodiment, the one or more promoters comprise Re. In another embodiment, the promoter includes Re and one or more species selected from Cs, K, Li, W, and S. In a further embodiment, the promoter includes Re and one or more species selected from Cs, Li, and S.

The catalyst that includes the carrier of the present disclosure may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm).

The transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

All of these promoters, aside from the alkali metals, can be in any suitable form, including, for example, as zerovalent metals or higher valent metal ions.

After impregnation with silver and any promoters, the impregnated carrier is removed from the solution and calcined for a time sufficient to reduce the silver component to metallic silver and to remove volatile decomposition products from the silver-containing carrier. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated carriers. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose.

During calcination, the impregnated carrier is typically exposed to a gas atmosphere comprising air or an inert gas, such as nitrogen. The inert gas may also include a reducing agent.

In another aspect, the present disclosure is directed to a method for the vapor phase production of ethylene oxide by conversion of ethylene to ethylene oxide in the presence of oxygen by use of the catalyst described above. Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. A typical process for the oxidation of ethylene to ethylene oxide comprises the vapor phase oxidation of ethylene with molecular oxygen in the presence of the catalyst of the present disclosure in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The catalysts containing the carrier of the present disclosure have been shown to be particularly selective catalysts in the oxidation of ethylene with molecular oxygen to ethylene oxide. Selectivity values of at least about 83 mol % up to about 93 mol % are typically achieved. In some embodiments, the selectivity is from about 87 mol % to about 93 mole %. The conditions for carrying out such an oxidation reaction in the presence of the catalyst of the present disclosure broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or by-products, unreacted materials are typically returned to the oxidation reactor. For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-350 kg EO per cubic meters of catalyst per hour. More typically, the feed composition at the reactor inlet comprises 1-40% ethylene, 3-12% oxygen, 0.3-40% $CO_2$, 0-3% ethane, 0.3-20 ppmv total concentration of organic chloride moderator, and the balance of the feed comprised of argon, methane, nitrogen, or mixtures thereof.

In other embodiments, the process of ethylene oxide production includes the addition of oxidizing gases to the feed to increase the efficiency of the process. For example, U.S. Pat. No. 5,112,795 discloses the addition of 5 ppm of nitric oxide to a gas feed having the following general composition: 8 volume % oxygen, 30 volume % ethylene, about 5 ppmw ethyl chloride, and the balance nitrogen.

The resulting ethylene oxide is separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, from about 0.3 to about 6, preferably from about 0.3 to about 2.0, volume percent.

Examples have been set forth below for the purpose of further illustrating the present disclosure. The scope of the present disclosure is not to be in any way limited by the examples set forth herein.

In the following examples, ZnO-modified alumina carriers were prepared in accordance with the present disclosure and were evaluated. ZnO was provided in form of an aqueous dispersion, which consisted of large agglomerates with sizes in the order of microns that contained approximately 30 nm primary ZnO crystallites. Alumina powder, ZnO, binders and fillers were mixed together to form an extrudeable paste. The extrudates were cut, dried, and subsequently sintered in air. Properties of the carrier compositions and processing details are provided in Table 1. Particles of the Zn—Al—O phase formed during sintering were uniformly dispersed on the alumina surfaces of the carriers. The surface coverage and distribution varied depending upon content of ZnO and the processing conditions. In order to at least partially remove the Zn—Al—O phase, the carrier was treated with multiple cycles of washing with concentrated NaOH (aq), which exposed cavities on the surfaces of the carrier.

TABLE 1

Properties of sintered carriers with introduced surface modifications using ZnO

| Carrier Composition | Filler content in wt % (organics + water)* | ZnO powder (wt %)* | Sintering Conditions | Water Absorption (%) | BET Surface Area (m²/g) | Average Crush Strength (lbs) |
|---|---|---|---|---|---|---|
| A | 63.3 | 7.7 | 1600° C.-12 hours | 50.4 | 0.56 | 9.5 |
| B | 55.0 | 7.7 | 1550° C.-12 hours | 39.2 | 0.79 | 9.9 |
| C | 52.0 | 5.0 | 1550° C.-12 hours | 41.3 | 0.81 | 10.2 |

*Calculated relative to the total weight of alpha alumina

Micro-reactor Test Runs

Figure 2A:
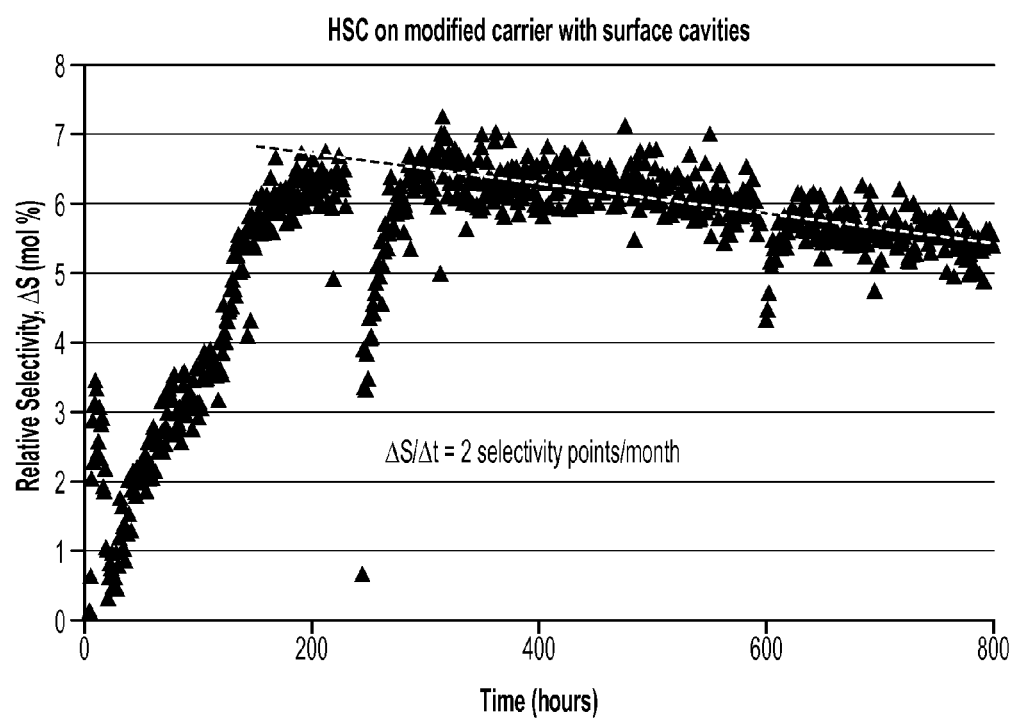
FIG. 2A is a graph showing the results of an accelerated ethylene epoxidation micro-reactor test performed on HSC deposited on a ZnO modified carrier (Composition A; inventive carrier).
Figure 2B:
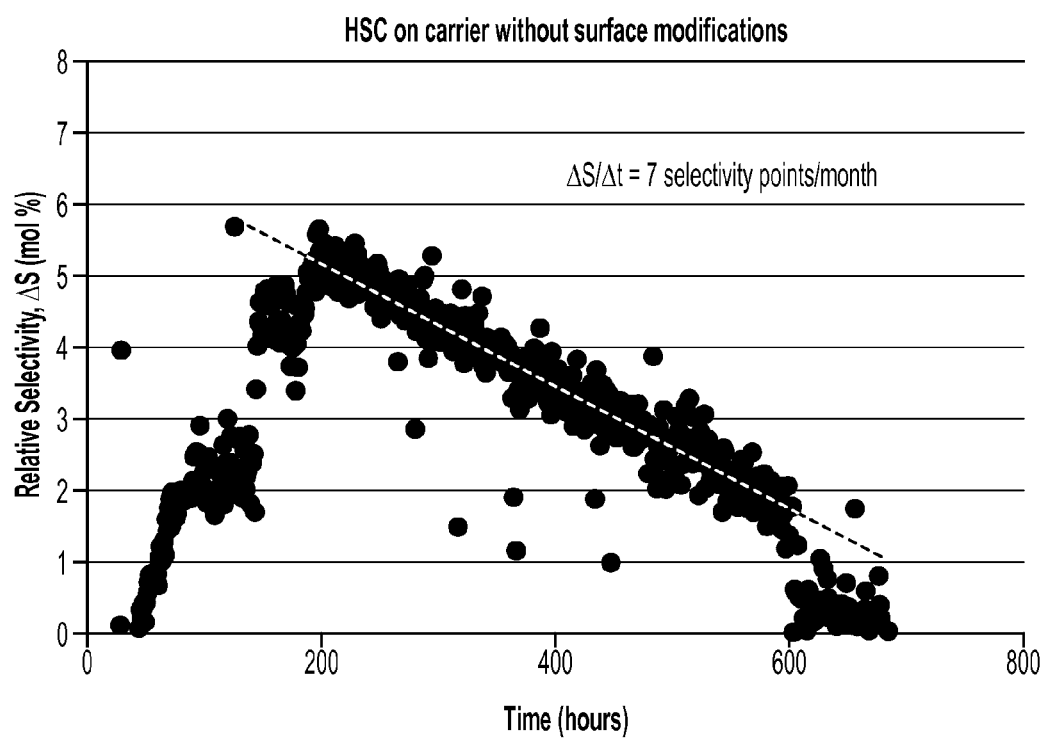
FIG. 2B is a graph showing the results of an accelerated ethylene epoxidation micro-reactor test performed on HSC deposited on carrier without any surface modification (prior art carrier and HSC).

Accelerated ethylene epoxidation micro-reactor tests were performed using gas feeds with the following concentrations: 15% ethylene, 7% oxygen, 2% $CO_2$, at temperatures ranging between 230° C. and 280° C. The tests were performed under the same conditions on HSC deposited on modified carrier Composition A with surface cavities (FIG. 2A), and for comparison on HSC deposited on support without any surface modifications (FIG. 2B).

Accelerated ethylene epoxidation micro-reactor tests on ZnO-modified carrier with surface cavities showed significantly improved catalyst stability. The selectivity decline rate ($\Delta S/\Delta t$) of this HSC was about 2 selectivity points per month (FIG. 2A). Conversely, the selectivity decline rate ($\Delta S/\Delta t$) of HSC deposited on support without any surface modifications was about 7 selectivity points per month (FIG. 2B). SEM analysis of the spent HSC after 800 hrs on feed revealed Ag particles trapped in multiple cavities of the surface-modified carrier, explaining enhanced stability.

While there have been shown and described what are presently believed to be the preferred embodiments of the present disclosure, those skilled in the art will realize that other and further embodiments can be made without departing from the spirit and scope of the present disclosure, and this disclosure includes all such modifications that are within the intended scope of the claims set forth herein.

What is claimed is:

1. A method of forming an alumina carrier, said method comprising:
    providing an admixture of reactive particles dispersed on a surface of alumina particles, wherein said reactive particles comprise a different material than said alumina particles;
    forming said admixture into a predetermined shape;
    sintering the admixture to form an alumina carrier having said predetermined shape and comprising sacrificial particles located on the surface and embedded within a portion of each alumina particle, wherein each sacrificial particle comprises a material containing an element of the reactive particle-Al—O, has a different phase than the alumina particles, and has a higher solubility in a solvent than the alumina particles; and
    removing at least a portion of said sacrificial particles from each of the alumina particles using the solvent to form cavities in the surface of each of the alumina particles.

2. The method of claim 1, wherein said providing the admixture comprises adding a dispersion of said reactive particles to said alumina particles.

3. The method of claim 1, wherein said reactive particles comprise metal oxide particles.

4. The method of claim 3, wherein said metal oxide particles are selected from the group consisting of zinc (Zn) oxide, calcium (Ca) oxide, magnesium (Mg) oxide, boron (B) oxide and mixtures thereof.

5. The method of claim 1, wherein said reactive particles comprise non-oxides selected from the group consisting of native metals, sulfides, sulfates, carbonates, carbides, nitrides and any combination thereof.

6. The method of claim 1, wherein from 1 to 10 weight percent of said reactive particles are dispersed on said surface of said alumina particles.

7. The method of claim 1, wherein said sintering is performed in air and at a temperature from 1000° C. to 1600° C.

8. The method of claim 1, wherein said solvent is an aqueous alkaline solvent or an aqueous acidic solvent.

9. The method of claim 1, wherein said reactive particles comprise zinc oxide and said sacrificial particles comprise a Zn—Al—O phase.

10. The method of claim 1, wherein each cavity has a diameter from 2 nm to 5 microns.

11. A method of forming a silver based ethylene oxide catalyst, said method comprising:
    forming an alumina carrier, wherein said forming said alumina carrier comprises:
    (i) providing an admixture of reactive particles dispersed on a surface of alumina particles, wherein said reactive particles comprise a different material than said alumina particles;
    (ii) forming the admixture into a predetermined shape;
    (iii) sintering the admixture to form an alumina carrier having said predetermined shape and comprising sacrificial particles located on the surface and embedded within a portion of each alumina particle, wherein each sacrificial particle comprises a material containing an element of the reactive particle-Al—O, has a different phase than the alumina particles, and has a higher solubility in a solvent than the alumina particles; and (iv) removing at least a portion of said sacrificial particles from each of the alumina particles using the solvent to form cavities in the surface of each of the alumina particles; and depositing silver on said alumina carrier, wherein said depositing comprises utilizing an impregnation solution containing from about 0.5% to 45% silver.

12. The method of claim 11, further comprising depositing a promoting amount of one or more promoters deposited on said alumina carrier, wherein said depositing said promoting amount of one or more promoters is performed prior to, coincident with, or after said depositing said silver on said alumina carrier.

13. The method of claim 11, wherein said reactive particles comprise metal oxide particles.

14. The method of claim 13, wherein said metal oxide particles are selected from the group consisting of zinc (Zn) oxide, calcium (Ca) oxide, magnesium (Mg) oxide, boron (B) oxide and mixtures thereof.

15. The method of claim 11, wherein said reactive particles comprise non-oxides selected from the group of native metals, sulfides, sulfates, carbonates, carbides, nitrides and any combination thereof.

16. The method of claim 11, wherein from 1 to 10 weight percent of said reactive particles are dispersed on said surface of said alumina particles.

17. The method of claim 11, wherein said sintering is performed in air and at a temperature from 1000° C. to 1600° C.

18. The method of claim 11, wherein said solvent is an aqueous alkaline solvent or an aqueous acidic solvent.

19. The method of claim 11, wherein said reactive particles comprise zinc oxide and said sacrificial particles comprise a Zn—Al—O phase.

20. A carrier comprising a plurality of bound alumina particles, wherein each alumina particle contains a plurality of cavities located within a surface of the alumina particle, and wherein each cavity has a diameter from 2 nm to 5 microns.

21. The carrier of claim 20 further comprising pores located between at least some of the alumina particles.

22. The carrier of claim 21, wherein said alumina particles comprise alpha-alumina particles.

23. The carrier of claim 21, wherein at least some of the cavities include a material having a different phase and solubility than said alumina particles embedded therein.

24. The carrier of claim 23, wherein said material comprises M-Al—O, wherein M is at least one of zinc (Zn), calcium (Ca), magnesium (Mg), and boron (B).

25. The carrier of claim 24, wherein M is Zn, and said material has a Zn—Al—O phase.

26. An ethylene epoxidation catalyst comprising:

a carrier comprising a plurality of bound alumina particles, wherein each alumina particle contains a plurality of cavities located within a surface of the alumina particle, and wherein each cavity has a diameter from 2 nm to 5 microns; and silver and a promoting amount of one or more promoters deposited on and/or in said carrier.

27. The catalyst of claim 26, wherein the one or more promoters is cesium.

28. The catalyst of claim 26, wherein the one or more promoters is potassium.

29. The catalyst of claim 26, wherein the one or more promoters is rhenium.

30. The catalyst of claim 29, further comprising a promoting amount of an alkali or alkaline earth metal.

31. The catalyst of claim 29, further comprising a promoting amount of at least one of cesium, lithium, tungsten, and sulfur.

32. The catalyst of claim 26 wherein said carrier further comprises pores located between at least some of the alumina particles.

33. The catalyst carrier of claim 26, wherein said alumina particles of said carrier comprise alpha-alumina particles.

34. The catalyst carrier of claim 26, wherein said carrier comprises non alpha-alumina particles.

35. The catalyst of claim 26, wherein at least some of the cavities of said carrier include a material having a different phase and solubility than said alumina particles embedded therein.

36. The catalyst of claim 35, wherein said material comprises M-Al—O, wherein M is at least one of zinc (Zn), calcium (Ca), magnesium (Mg), and boron (B).

37. The catalyst of claim 36, wherein M is Zn, and said material has a Zn—Al—O phase.

* * * * *